United States Patent [19]

English

[11] Patent Number: 5,173,409
[45] Date of Patent: Dec. 22, 1992

[54] RECOVERY OF BT ENDOTOXIN PROTEIN FROM LYSED CELL MIXTURES

[75] Inventor: Leigh H. English, Holland, Pa.

[73] Assignee: Ecogen Inc., Langhorne, Pa.

[21] Appl. No.: 447,966

[22] Filed: Dec. 8, 1989

[51] Int. Cl.$^5$ .................. C12P 21/04; C12R 1/07
[52] U.S. Cl. .................. 435/71.1; 435/71.2; 435/71.3; 435/252.31; 435/252.5; 435/803; 435/832
[58] Field of Search ............ 435/71.1, 71.2, 71.3, 435/252.5, 252.31, 832, 803

[56] References Cited

PUBLICATIONS

Bietlot et al., *Biochem. J. (1989)* 260:87–91.
Höfte et al., *Microbiol. Rev.* (1989) 53:242–255.
Zhu et al., *Appl. Environ. Microbiol.* (1989) 55:1279–1281.
Aronson et al., *Appl. and Environ. Microbiol.* (1987) 53:416–421.
Tyski et al., *Biochem. Biophys. Res. Commun.* (1986) 141:106–111.
Höfte et al., *Eur. J. Biochem.* (1986) 161:273–280.
Huber-Lukac et al., *Infect. Immun.* (1983) 40:608–612.
Nickerson et al., *Europ. J. Appl. Microbiol. Biotechnol.* (1981) 13:213–215.
Bulla et al., *J. Biol. Chem.* (1981) 256:3000–3004.
Lilley et al., *J. Gen. Microbiol.* (1980) 118:1–11.
Fast et al., *Biochem. Biophys. Res. Commun.* (1980) 95:1314–1320.
Bulla et al., *Biochem. Biophys. Res. Commun.* (1979) 91:1123–1130.
Ang et al., *Appl. Environ. Microbiol.* (1978) 36:625–626.
Milne et al., *J. Invert. Path. (1977)* 29:230–233.
Chestukhina et al., translation from Biokhimiya (1977) 42:1660–1667.

*Primary Examiner*—Herbert J. Lilling
*Attorney, Agent, or Firm*—Christopher Egolf; Alan S. Nadel

[57] ABSTRACT

Purified endotoxin protein is recovered from aqueous suspensions containing lysed cells and *Bacillus thuringiensis* crystalline endotoxin protein in a multistep process.

The aqueous suspension, e.g., a concentrated fermentation culture, is first treated under strongly basic or acidic conditions to solubilize the crystal protein and the solution is then separated from residual solids. Endotoxin protein is precipitated from the separated aqueous solution, by adjusting its pH to the isoelectric point of the protein, and recovered by centrifugation or the like.

25 Claims, No Drawings

RECOVERY OF BT ENDOTOXIN PROTEIN FROM LYSED CELL MIXTURES

BACKGROUND OF THE INVENTION

1. Field of the Invention

This invention relates to a method for recovering *Bacillus thuringiensis* crystal protein from an aqueous fermentation culture containing lysed cells, spores and insecticidal crystal protein.

2. Description of the Prior Art

*Bacillus thuringiensis* (Bt) is a well known bacterium characterized by its ability to produce crystal protein inclusions during its sporulation phase. Many of these specific insecticidal activity. An excellent review, "Insecticidal Crystal Proteins of *Bacillus thuringiensis*", has been published by Hofte et al. in Microbiol.Rev. (1989) 53:242-252.

Insecticidal compositions containing sporulated Bt, i.e., lysed *Bacillus thuringiensis* cells, spores, and crystal proteins, in spent fermentation culture used to prepare such Bt's, are sold commercially for insect pest control. Improved formulations, containing only the insecticidal crystal protein in combination with agriculturally-acceptable adjuvants for topical application to the desired plant, soil or other locus, are desirable for several reasons: Concentration levels of the crystal protein, including combinations of crystal proteins, may be precisely controlled. Impurities, spores, Bt cell debris, and spent fermentation media components would be absent from the formulations.

Production of such improved insecticidal formulations requires commercial quantities of crystal protein in relatively pure form. Most of the protein purification techniques described in the literature are laboratory methods for small scale preparation of Bt endotoxin protein. These Bt protein recovery or purification techniques are generally costly, complex, and have low recovery yields.

Density gradient centrifugation has been used for the physical separation of Bt crystal protein from lysed cells, spores, and other solids in a spent fermentation medium, based on the different densities of these components. Density gradient centrifugation techniques are described by Nickerson et al., *Europ.J.Appl.Microbiol.-Biotechnol.* (1981) 13:213-215 (using sodium bromide), and by Milne et al., *J.Invert.Path.* (1977) 29:230-232 (using Renografin). Density gradient separations generally require the use of expensive materials as the separation medium, and the recovered crystal protein often requires further purification to remove associated impurities not removeable by washing.

Other laboratory techniques for isolation of Bt crystal protein involve solubilization of the crystal protein by various means and purification of the solubilized protein by ion exchange chromatography or gel filtration chromatography. These latter procedures are not ordinarily suitable for large scale, commercial purification of Bt endotoxin protein, primarily because of their high cost and low recovery yields. Aronson et al., *Appl.Environ. Microbiol.* (1987) 53:416-421, digest Bt proteins from a fermentation powder with trypsin at pH 9 and precipitate the digested protein with ammonium sulfate. After the precipitated protein is redissolved at pH 9.5 in buffered solution, it is purified further using ion exchange and hydrophobic-interaction chromatography. Tyski et al., *Biochem.Biophys.Res.Comm.* (1986) 141:106-111, extract Bt crystal protein obtained from a fermentation culture with bicarbonate buffer at pH 9 containing a reducing agent. The solubilized protein is precipitated with ammonium sulfate, then resolubilized and proteolytically digested with trypsin in a buffered solution at pH 8. The digested protein is next purified by ion exchange chromatography. Hofte et al., *Eur.J.Biochem.* (1986) 161:273-280, use either bicarbonate extraction buffer at pH 9.5 or TRIS-HCl-containing and urea-containing buffer at pH 8 (both with protein reducing agent) to solubilize the crystal protein. The solubilized protein is purified further by anion exchange or gel filtration chromatography.

Bulla et al., *J.Biol.Chem.* (1981) 256:3000-3004, and *Biochem.Biophys.Res.Comm.* (1979) 91:1123-1130, utilize sodium hydroxide at pH 12 for solubilization of Bt crystal protein obtained by density gradient centrifugation. The solubilized protein is purified further using gel filtration chromatography. Lilley et al., *J.Gen.Microbiol.* (1980) 118:1-11, dissolve partially-purified protein crystals in an alkaline buffer at pH 10.5 containing a reducing agent, followed by digestion of the solubilized protein with trypsin and other proteolytic enzymes. A trypsin-resistant protein is purified further by gel filtration and ion exchange chromatography.

The present invention provides a straight forward method of purifying Bt crystal protein without resorting to density gradient centrifugation, ion exchange chromatography, gel filtration chromatography, molecular sieve filtration, or other costly separation techniques utilized in the prior art. The method of this invention recovers a purified endotoxin protein in good yields and without significant loss of the protein toxin's insecticidal activity.

In this disclosure, the terms "crystal protein", "crystal" or "crystalline endotoxin protein", "protein endotoxin" or "toxin", and "Bt toxin" are used synonomously to refer to Bt-type endotoxin protein. Such endotoxin protein may be in protoxin form or activated form, unless indicated otherwise.

SUMMARY OF THE INVENTION

In accordance with the present invention, *Bacillus thuringiensis* endotoxin protein is recovered from an aqueous suspension containing the crystalline protein by the process of treating an aqueous suspension containing lysed cells and *Bacillus thuringiensis* crystalline endotoxin protein under substantially nonneutral pH conditions to induce solubilization of the crystalline protein via hydration of the charges on the protein; separating aqueous solution from solid matter in the treated aqueous suspension; adjusting the pH of the separated aqueous solution to a value that is substantially equivalent to the isoelectric point of the endotoxin protein, to induce precipitation of the protein from solution; and recovering the precipitated endotoxin protein.

The process of this invention is applicable to the known types of Bt endotoxin proteins, in particular, CryI, CryII, CryIII and CryIV proteins. The process is especially useful for recovering such Bt endotoxin proteins from concentrated fermentation cultures of sporulated Bt cells. The resulting Bt endotoxin proteins are essentially free of any of the contaminants originally present in the spent fermentation culture, e.g., Bt spores.

A preferred embodiment of this invention utilizes a base at alkaline pH, above about 9.5 and preferably at about pH 12, in the protein solubilization step.

For endotoxin proteins other than CryI proteins, another embodiment of this invention utilizes an acid in lieu of the base in the protein solubilization step, at a pH of less than 5 and preferably within the pH range 2-4.

In a preferred embodiment of this invention specifically applicable to CryI-type endotoxin proteins, Bt CryI endotoxin protein is recovered in the activated toxin form from an aqueous suspension containing the crystalline protein by the process of treating an aqueous suspension containing lysed cells and *Bacillus thuringiensis* crystalline CryI endotoxin protein in protoxin form with a base at an alkaline pH, above about 9.5, to effect solubilization of the crystalline protein;

separating aqueous solution from solid matter in the treated aqueous suspension;

activating the solubilized endotoxin protein in the separated aqueous solution with a protease introduced into the solution, at a pH at which the protease is proteolytically active;

adjusting the pH of the separated aqueous solution to a value that is substantially equivalent to the isoelectric point of the endotoxin protein in activated toxin form, to induce precipitation of the protein from solution; and recovering the precipitated CryI endotoxin protein in activated toxin form.

The protein endotoxin activation step and protein purification step are preferably carried out concurrently in this latter embodiment. This is accomplished by introducing the activation protease into the aqueous solution at a pH value substantially equivalent to the pH value of the endotoxin protein in activated toxin form, preferably using trypsin as the protease at or about pH 7-8.

Another embodiment of this invention includes the *Bacillus thuringiensis* endotoxin protein products made by the protein recovery processes described above. These Bt endotoxin protein products are useful in insecticidal compositions formulated with an agriculturally-acceptable carrier.

Detailed Description

The process of this invention is applicable to recovery of *Bacillus thuringiensis* endotoxin protein on a small scale in a laboratory or the like, or to recovery of commercial scale quantities of the protein. Large scale recovery of the protein by this process permits the formulation of biological insecticides that contain the Bt endotoxin protein but that are essentially free of Bt spores, lysed cell debris, and spent fermentation medium components.

This invention provides a means for the straightforward recovery of crystalline Bt endotoxin protein of known types: CryI crystal protein (formerly designated P-1 protein), CryII crystal protein (formerly P-2 or CryB protein), CryIII (formerly CryC protein) and CryIV (formerly CryD protein). The process may be used to recover individual proteins of any of these types from aqueous suspensions containing the crystalline Bt endotoxin as the sole protein. Mixtures of several Bt endotoxin proteins are also amenable to recovery by this invention.

Mixtures of these proteins are ordinarily recovered as mixtures of the same proteins, albeit purified of the unwanted components normally associated with the spent fermentation culture used to produce the proteins. CryI protein, however, contained in admixture with CryII or other Bt endotoxin proteins may be recovered separately by first precipitating the other toxins at their isoelectric points of about pH 7-8 and then recovering the CryI protein in protoxin form, at its isoelectric point of pH 5.5.

The protein recovery method of this invention is applicable to virtually any aqueous suspension that contains lysed cells and crystalline Bt endotoxin protein. The source of the aqueous suspension is not critical and is ordinarily a spent fermentation culture containing lysed cells that were responsible for production of the crystal protein. The lysed cells are usually sporulated *Bacillus thuringiensis* cells but may also be nonsporulating *Bacillus thuringiensis* strains. However, Bt endotoxin protein may also be produced by other *Bacillus* species (*B. megaterium* or *B. subtilis*) or by *E.coli,* any of which can be transformed with a vector containing one or more genes coding for Bt endotoxin protein.

If the cells in the spent fermentation culture or other aqueous suspension have not lysed spontaneously, e.g., during sporulation for spore-producing Bt strains, then the crystal protein-containing cells may be lysed by conventional methods, by mechanical stress or by the action of detergents.

As a preliminary and optional step to the process of this invention, the aqueous suspension containing lysed cells and crystalline Bt endotoxin protein may be centrifuged, or filtered, and washed with water. The washing step serves to remove soluble matter from the concentrated centrifuge cake, e.g., fermentation components. This procedure improves the likelihood of recovering relatively pure Bt endotoxin protein via the process of this invention.

The aqueous suspension containing the lysed cells and crystal protein is preferably in concentrated form, rather than being a dilute suspension, prior to its being treated according to this invention. This is the case regardless of whether the optional water washing step is carried out.

Solubilization of the crystal protein in the process of this invention is achieved by treating the aqueous suspension containing the crystal protein under substantially nonneutral pH conditions, i.e., strongly alkaline or strongly acidic conditions. Such pH conditions cause the charges on the protein to become hydrated, thereby effecting solubilization of the protein.

Alkaline solubilization is preferred, and any number of bases are suitable for this purpose. Alkali metal hydroxide and alkaline earth metal hydroxides may be used; potassium hydroxide is preferred among the former group of bases. Ammonium hydroxide is also suitable, and this base may be preferred for large scale protein recovery processes where recovery and/or recycle of the salt produced by this process is a consideration.

Protein solubilization under alkaline pH conditions is generally carried out at a pH above 9.5, preferably at about pH 12. Solubilization pH values above about 13 are best avoided or at least minimized in duration of time, to prevent degradation of the solubilized protein.

In lieu of a base, the protein solubilization step may also be affected under acidic pH conditions, using an acid. The protein solubilization step under strongly acidic conditions may be employed with CryII, CryIII and/or CryIV endotoxin proteins. The procedure is not ordinarily effective for use with CryI-type endotoxin proteins.

Suitable acids include those that are not adversely reactive with the endotoxin protein. Such acids may be selected from the group of acetic acid, boric acid, citric acid, hydrochloric acid, lactic acid, oxalic acid, sulfuric acid, and sulfurous acid.

The pH during acidic protein solubilization is generally less than about 5 and is preferably adjusted within the pH range of about 2-4.

Complete solubilization of the protein is ordinarily achieved in a relatively short time, on the order of minutes, e.g., less than ten to fifteen minutes and usually less than five minutes. This is the case whether solubilization is effected under alkaline or acidic pH conditions.

Protein solubilization rate may be increased by providing moderate agitation of the base- or acid-treated aqueous suspension. The solution temperature during solubilization is not critical. Elevated temperatures, above 25°-30° C., e.g., about 50° C., increase the solubilization rate but may also promote protein degradation, via proteolytic action of proteases naturally present in the spent fermentation culture.

Protein solubilization rate may also be increased by the addition of a protein reducing agent to reduce disulfide bridges in the crystal protein being solubilized. Such protein reducing agents are well known and include, for example, mercaptoethanol, dithiothreitol, thioglycolic acid, and the like.

Following complete solubilization of the protein, the aqueous solution is separated from the remaining solid matter, e.g., cell debris and spores, by conventional solids-liquids separation techniques. Centrifugation and filtration are suitable separation methods. Filtration is generally preferred for removing spores that may remain suspended in the aqueous medium, even after centrifugation. Filter media with 0.45 $\mu$m openings are normally adequate for removing Bt spores from the aqueous solution.

At this point, the concentration of total solubilized protein in the separated aqueous solution may optionally be determined by conventional methods, e.g., the bicinchonic acid binding protein analysis described by Smith et al., *Anal.Biochem.* (1986) 150:76-85. This information is useful for calculating the amount of protease to be employed, in the embodiment of this invention which recovers CryI crystal protein in activated form.

The solubilized Bt endotoxin protein is recovered via precipitation from the aqueous solution by adjusting the pH of the (alkaline or acidic) aqueous solution to a value substantially equivalent to the isoelectric point of the endotoxin protein. This protein precipitation carried out within the temperature range of 15°-35° C. and is preferably within the range of 15°-25° C.

This pH adjustment may be accomplished by introducing an acid (to the alkaline aqueous solution) or a base (to the acidic aqueous solution). This solution is preferably agitated during this procedure. The introduced acid or base is preferably buffered to maintain the pH of the treated medium close to the desired isoelectric point pH value. At this isoelectric point pH value, the endotoxin protein precipitates from solution, permitting recovery of an uncontaminated Bt endotoxin protein.

The isoelectric point for CryII, CryIII and CryIV-type endotoxin proteins is about pH 7.5. CryI proteins exist in two forms, each having a unique isoelectric point. The isoelectric point for CryI-type endotoxins is about pH 7.5 for the toxin in activated form, and about pH 5.5 for the toxin in protoxin form.

CryI endotoxin protein, it should be noted, is produced by the Bt or other transformed microorganism in a protoxin form. The protein must be proteolytically degraded, with enzymes that are normally present in the midgut of the insect(s) susceptible to such toxin proteins, before the protein, in activated toxin form, is insecticidal to the insect. The present invention provides for recovery of CryI proteins in either protoxin or activated toxin form. In the latter case, the recovery process includes an activation step, utilizing a protease such as trypsin, to convert the solubilized CryI protoxin protein to the activated toxin form.

Recovery of CryI endotoxin protein in protoxin form is carried out as described above, by solubilizing the crystal protein under highly alkaline conditions and inducing precipitation of the protoxin at its isoelectric point value of about pH 5.5. During the protein solubilization step, the pH is desirably maintained at about 13 to suppress the action of proteases that are naturally associated with the crystal protein in the fermentation culture. Exposure time of the solubilized protein to these highly alkaline pH conditions should be kept short, under five minutes if possible, to minimize alkali-induced degradation of the protein. This may be accomplished by quickly separating the alkaline aqueous solution from the solid matter in the suspension and promptly adjusting the pH of the separated aqueous solution to the CryI protein protoxin's isoelectric point.

Recovery of CryI endotoxin protein in activated toxin form is carried out as described previously, but with the addition of a protein activation step. Following alkaline solubilization of the crystal protein and separation of the aqueous solution from the treated aqueous suspension, the solubilized CryI endotoxin protein is activated with a protease. The protease may be introduced directly into the solution, e.g., via addition of trypsin or other protease. The protease may alternatively be introduced indirectly, as proteases that are naturally present on or associated with the crystal protein when it is solubilized. The addition of external proteases is preferred since this ensures reliability of protein activation.

The solution pH should be maintained at a value that is conducive to proteolytic action by the protein enzyme, i.e., not highly alkaline or acidic. The pH value of the solution is preferably within the range of 6-8, more preferably 7-8, during the CryI protein activation step.

The amount of protease, temperature of the solution, and duration of the activation step are not critical. A solution temperature within the range of 15°-25° C. is satisfactory. Agitation during the activation step is desirable to ensure rapid proteolytic action, on the order of seconds or a few minutes.

The CryI protein activation step may be carried out prior to the protein precipitation step or, more preferably, concurrently with the protein precipitation step. In the latter case, the activation protease is introduced into the separated aqueous solution (from the protein solubilization step) at a pH value that is substantially equivalent to the pH value of the endotoxin protein in activated toxin form. The solution pH during the simultaneous protein activation/protein precipitation steps is preferably about pH 7-8. The preferred protease is trypsin.

Because the protoxin form of CryI endotoxin protein has an isoelectric value that is relatively acidic, about pH 5.5, the protoxin form remains solubilized during this concurrent protein activation/precipitation procedure. The solution during this procedure is maintained at a pH of about 7-8, which is substantially equivalent to the isoelectric point (about pH 7.5) of the CryI protein in activated form. Only upon proteolytic conversion of the protoxin form to the activated form is the solubilized CryI endotoxin protein capable of precipitating from solution.

The precipitated endotoxin protein obtained with any of the procedures described above is recovered by conventional solids-liquid separation techniques. Centrifugation and filtration are suitable methods. Additional recovery of protein remaining solubilized in the solution can be obtained by cooling the solution to reduce protein solubility. The solution may be cooled to its freezing point, if desired, to increase recovery of precipitated endotoxin protein.

The endotoxin protein recovered by the process of this invention is relatively pure and is essentially free of any contaminants originally present in the aqueous suspension, e.g., cell debris, spores, spent fermentation media components and other fermentation by-products. Furthermore, the recovered toxin protein exhibits no significant loss of insecticidal activity and is obtained in good recovery yields.

The Bt endotoxin protein products obtained by the protein recovery process of this invention are especially useful in agricultural formulations, intended for the control of insects susceptible to these crystal proteins. The products of the various processes described above may be formulated with agriculturally-acceptable carriers to provide insecticidal compositions. These compositions are noteworthy for the absence of any contaminants, e.g., Bt spores originally present in the spent fermentation culture containing the Bt endotoxin protein and treated by the process of this invention.

EXAMPLES

The process of this invention, as applied to recovery of CryI endotoxin protein in activated toxin form and, alternatively, in protoxin form, is illustrated in the following examples.

EXAMPLE 1

The protocol described in this Example 1 provides for recovery of a *Bacillus thuringiensis* CryI-type endotoxin protein, in activated toxin form, from a fermentation culture of lysed cells.

The fermentation culture is spent fermentation medium containing lysed microorganism cells and CryI crystal protein made by such microorganisms. The microorganisms are typically sporulated *Bacillus thuringiensis* but may also be other *Bacillus* strains or *E.coli* transformed with toxin genes coding for CryI endotoxin protein.

CryI endotoxin protein normally present in the lysed cell mixture as crystalline protein in protoxin form. The protocol of this Example includes a step for activation of the protoxin protein during recovery of the CryI endotoxin protein.

The procedure employs a base, potassium hydroxide, to effect solubilization of the crystalline CryI protein at a pH of about 12.

The CryI endotoxin protein is precipitated from solution by adjusting the solution pH to the isoelectric point of the activated CryI protein, a pH of about 7.5. The protein precipitation step and protein activation step are carried out concurrently, by introducing the activation protease, trypsin, into the aqueous solution containing the solubilized protein at the isoelectric point pH value of the activated protein. The protoxin form of CryI endotoxin protein, it should be noted, has an isoelectric point of less than pH 6. Consequently, only the activated form of the CryI endotoxin protein can precipitate when the alkaline aqueous solution is adjusted to a substantially neutral pH and treated with trypsin.

Enhanced recovery of the activated CryI endotoxin protein is obtained by cooling the suspension to reduce the protein solubility in the aqueous medium.

The protocol, intended for small scale protein recoveries, is as follows:

1. A spent fermentation culture, containing lysed *Bacillus thuringiensis* cells comprising crystalline CryI protein, spores and cell debris, is first concentrated by centrifugation, e.g., 7000 xg for twenty minutes in a laboratory centrifuge.
2. The concentrated solids are separated from the supernatant liquor by decanting and are washed in an excess of water to dissolve soluble contaminants present in the solids. This may be accomplished by resuspending the pelleted solids in water at 15°-25° C. with vigorous stirring using a magnetic stir bar to disperse the solids; the volume ratio of water:solids may be 5000:1.
3. The resuspended solids are centrifuged, as before in step 1, and the washed solids separated from the wash water by decanting.
4. The washed solids are introduced into an aqueous alkaline solution at ambient temperature containing potassium hydroxide and a protein reducing agent (12 mM KOH, 1 mM dithiothreitol, pH 12) to reduce disulfide bonds and thereby facilitate solubilization; the volume ratio should be about 10:1 solution:solids. The pH should be checked and adjusted, as necessary, to pH 12 with additional solution (12 mM KOH, 1 mM dithiothreitol).
5. The aqueous medium containing the suspended solids is then incubated at a temperature of 50° C. for ten minutes, without agitation, to complete solubilization of the CryI endotoxin protein.
6. The aqueous medium is brought to ambient temperature and centrifuged, as before in step 1, and the supernatant solution is recovered by filtration through a 0.45 μm filter to remove contaminating spores still suspended in the solution.
7. At this point, the separated aqueous solution is assayed for total solubilized protein content, e.g., by the method of Smith et al., *Anal.Biochem.* (1986) 150:76-85; this information is used in steps 9 and 10.
8. The pH of the separated aqueous solution is adjusted to pH 7.5 by the addition of an equal volume of buffered solution (imidazole-HCl pH 7.5), at a temperature of about 20°-25° C.
9. The concentration of solubilized protein in the pH-adjusted solution of step 8 is reduced, as necessary with dilution water, to a value of 1 mg/ml or slightly less.
10. The solubilized protein in the aqueous solution of step 9 is converted from protoxin to activated toxin form by the addition of L-1-tosylamide-2-phenylethylchloromethylketone trypsin, in a weight ratio of 0.02:1 trypsin:protein. This step initiates precipitation of CryI endotoxin protein, in activated form, from the solution.
11. The trypsin-treated aqueous suspension is maintained at a temperature of about 22°-25° C., with moderate stirring, for fifteen minutes.
12. The aqueous suspension is then cooled to freezing temperature in a dry ice-acetone bath, thawed as necessary, and centrifuged, e.g., 7000 xg for twenty minutes in a laboratory centrifuge, to concentrate the precipitated, activated CryI endotoxin protein.

13. The precipitated CryI endotoxin protein solids are then separated from the aqueous solution by decanting and may be washed with water, if desired. The recovered solids are CryI endotoxin protein, in activated form, essentially free of any contaminants in the original fermentation culture (e.g., spores, cell debris, spent fermentation media).

EXAMPLE 2

The protocol in this Example 2 differs from that of Example 1 in that a *Bacillus thuringiensis* CryI-type endotoxin protein is recovered in protoxin form, rather than in the activated toxin form. For this reason, the protein activation step with trypsin Example 1 is omitted from the Example 2 protocol.

As in Example 1, the procedure employs a potassium hydroxide to effect solubilization of the crystalline CryI protein under alkaline conditions, but this Example utilizes a more highly alkaline solubilization pH through use of a more concentrated base. This solubilization pH of 13 (compared to pH 12 in Example 1) also serves to inhibit the action of proteases which are naturally associated with the crystal protein in the fermentation culture and which would otherwise proteolytically degrade the protoxin.

Exposure of the solubilized protein to these highly alkaline conditions is kept short to minimize any alkali-induced degradation of the solubilized endotoxin protein. Precipitation of the CryI endotoxin in protoxin form is induced at the isoelectric point of the protoxin, a pH of about 5.5.

In other respects, the protocol of this Example 2 is similar to that of Example 1. The protocol has the following steps.

1. A spent fermentation culture, containing lysed *Bacillus thuringiensis* cells comprising crystalline CryI protein, spores and cell debris, is first concentrated by centrifugation, e.g., 7000 xg for twenty minutes in a laboratory centrifuge.
2. The concentrated solids are separated from the supernatant liquor by decanting and washed in an excess of water to dissolve soluble contaminants present in the solids. This may be accomplished by resuspending the pelleted solids in water at 15°–25° C. with vigorous stirring using a magnetic stir bar to disperge the solids; the volume of water:solids may be 5000:1.
3. The resuspended solids are centrifuged, as before in step 1, and the washed solids separated from the wash water by decanting.
4. The washed solids are introduced into an aqueous alkaline solution at ambient temperature, about 20°–25° C., containing potassium hydroxide (0.1 M KOH, pH 13); the volume ratio should be about 10:1 solution:solids.
5. The aqueous medium containing the suspended solids is mixed with a Vortex Genie 2 mixer for one minute, to complete solubilization of the CryI endotoxin protein.
6. The aqueous medium is centrifuged, as before in step 1, and the supernatant solution is recovered by filtration through a 0.45 μm filter to remove contaminating spores still suspended in the solution.
7. The pH of the separated aqueous solution is reduced to pH 5.5 by first introducing (with agitation) one volume of 0.1 M HCl (equal to the volume of separated aqueous solution) and then introducing two volumes of buffered solution, 50 mM 2-[N-morpholino]ethane sulfonic acid, pH 5.5. This step initiates precipitation of CryI endotoxin protein, in protoxin form, from the solution. The temperature of the solution during the acid addition should be maintained at ambient temperature, about 20°–25° C.
8. The aqueous suspension is then cooled to freezing temperature in a dry ice-acetone bath, thawed as necessary, and centrifuged, e.g., 7000 xg for twenty minutes in a laboratory centrifuge, to concentrate the precipitated CryI endotoxin protein.
9. The precipitated CryI endotoxin protein solids are then separated from the aqueous solution by decanting and may be washed with water, if desired. The recovered solids are CryI endotoxin protein, in protoxin form, essentially free of any contaminants in the original fermentation culture (e.g., spores, cell debris, spent fermentation media).

What is claimed is:

1. A process for recovering a *Bacillus thuringiensis* crystalline endotoxin protein from an initial aqueous suspension comprising lysed cells, the crystalline endotoxin protein and contaminants, which consists essentially of the following steps:
   (a) solubilizing the endotoxin protein by treating the initial aqueous suspension under substantially non-neutral pH conditions, resulting in (i) a soluble fraction consisting essentially of an aqueous solution containing the solubilized endotoxin protein and (ii) and insoluble fraction containing solid matter;
   (b) separating the soluble fraction from the insoluble fraction;
   (c) precipitating the solubilized endotoxin protein by adjusting the pH of the soluble fraction to a value that is substantially equivalent to the isoelectric point of the endotoxin protein; and
   (d) recovering the precipitated endotoxin protein, essentially free of the contaminants present in the initial aqueous suspension.

2. The process of claim 1 wherein the protein solubilization step (a) is carried out with a base, wherein the pH is adjusted above about 9.5.

3. The process of claim 2 wherein the pH during the protein solubilization step (a) is adjusted to a pH value of at least about 12.

4. The process of claim 2 wherein the base is selected from the group of alkali metal hydroxides, alkaline earth metal hydroxides and ammonium hydroxide.

5. The process of claim 1 wherein the crystalline endotoxin protein is selected from the group of CryII, CryIII and CryIV endotoxin proteins and the protein solubilization step (a) is carried out with an acid at a pH of less than about 5.

6. The process of claim 5 wherein the pH during the protein solubilization step (a) is adjusted to a pH of about 2–4.

7. The process of claim 5 wherein the acid is selected from the group of acetic acid, boric acid, citric acid, hydrochloric acid, lactic acid, oxalic acid, sulfuric acid and sulfurous acid.

8. The process of claim 1 wherein the crystalline endotoxin protein is a CryI protein and the protein is recovered in the protoxin form at an isoelectric point pH value of about 5.5.

9. The process of claim 1 wherein the crystalline endotoxin protein is selected from the group of CryII, CryIII and CryIV endotoxin proteins and the protein is recovered at an isoelectric point pH value of about 7.5

10. A process for recovering a *Bacillus thuringiensis* CryI endotoxin protein in activated toxin form from an initial aqueous suspension comprising lysed cells, the crystalline endotoxin protein in protoxin form and contaminants, which consists essentially of the following steps:
   (a) solubilizing the endotoxin protein by treating the initial aqueous suspension with a base to adjust the pH above about 9.5, resulting in (i) a soluble fraction consisting essentially of an aqueous solution containing the solubilized endotoxin protein and (ii) an insoluble fraction containing solid matter;
   (b) separating the soluble fraction from the insoluble fraction;
   (c) producing an endotoxin protein in active toxin form in the separated soluble fraction by adjusting the pH of the separated soluble fraction so that a protease present in the separated soluble fraction becomes proteolytically active;
   (d) precipitating the activated toxin form of the solubilized endotoxin protein by adjusting the pH of the soluble fraction to a value that is substantially equivalent to the isoelectric point of the endotoxin protein in activated form; and
   (e) recovering the precipitated CryI endotoxin protein in activated toxin form, essentially free of contaminants present in the initial aqueous suspension.

11. The process of claim 10 wherein the pH during the protein solubilization step (a) is adjusted to a pH value of about 12.

12. The process of claim 10 wherein the base is selected from the group of alkali metal hydroxides, alkaline earth metal hydroxides, and ammonium hydroxide.

13. The process of claim 10 wherein the CryI endotoxin is recovered in activated toxin form at an isoelectric point pH value of about 7.5.

14. The process of claim 10 wherein the protein activation step (c) and protein precipitation step (d) are carried out concurrently, by introducing the activation protease into the soluble fraction at a pH value substantially equivalent to the isoelectric point of the endotoxin protein in activated toxin form.

15. The process of claims 10 or 14 wherein the protein endotoxin activation step (c) is carried out at a pH of about 7-8.

16. The process of claims 10 or 14 wherein the protein endotoxin activation step (c) is carried out with trypsin as the protease.

17. The process of claim 10 wherein the protein endotoxin activation step (c) is carried out with protease contaminants that are associated with the crystalline endotoxin protein in the aqueous suspension.

18. The process of claim 10 wherein the protein endotoxin activation step (c) is carried out at a temperature which promotes proteolytic activity of the protease.

19. The process of claim 10 wherein the protein endotoxin activation step (c) is carried out at a temperature of about 15°-25° C.

20. The process of claims 1 or 10 wherein the initial aqueous suspension containing lysed Bt cells is a concentrated fermentation culture of sporulated *Bacillus thuringiensis* cells.

21. The process of claims 2 or 10 wherein the protein solubilization step (a) and the subsequent soluble fraction separation step (b) are carried out rapidly, to minimize exposure of the solubilized endotoxin protein to nonneutral pH conditions.

22. The process of claim 21 wherein the two steps (c) and (d) are carried out in less than about fifteen minutes.

23. The process of claim 1 wherein the separation step (b) and the recovery step (d) are accomplished via centrifugation or filtration.

24. The process of claim 10 wherein the separation step (b) and the recovery step (e) are accomplished via centrifugation or filtration.

25. The process of claim 10 further comprising a step between steps (b) and (c) of introducing a protease into the separated soluble fraction.

* * * * *